(12) United States Patent
Kakushadze

(10) Patent No.: US 10,685,738 B1
(45) Date of Patent: Jun. 16, 2020

(54) CANCER DIAGNOSTIC TOOL USING CANCER GENOMIC SIGNATURES TO DETERMINE CANCER TYPE

(71) Applicant: Quantigic Genomics LLC, Stamford, CT (US)

(72) Inventor: Zurab Kakushadze, Brooklyn, NY (US)

(73) Assignee: Quantigic Genomics LLC, Stamford, CT (US)

(*) Notice: Subject to any disclaimer, the term of this patent is extended or adjusted under 35 U.S.C. 154(b) by 526 days.

(21) Appl. No.: 15/709,407

(22) Filed: Sep. 19, 2017

(51) Int. Cl.
*G16B 20/00* (2019.01)
*G01N 33/574* (2006.01)
*G16B 25/00* (2019.01)
*G16B 30/00* (2019.01)
*G16B 40/00* (2019.01)

(52) U.S. Cl.
CPC ........ *G16B 20/00* (2019.02); *G01N 33/57484* (2013.01); *G16B 25/00* (2019.02); *G16B 30/00* (2019.02); *G16B 40/00* (2019.02)

(58) Field of Classification Search
CPC .... G06Q 10/0635; G06N 20/00; G06N 7/005; G06N 3/08; A61B 5/00; A61B 5/7267; G16H 10/40; G16H 10/60; G16H 50/20; G16H 50/30; G16H 50/70; G01N 2800/56; G01N 2800/7028; G01N 30/8686; G01N 33/2882; G01N 33/5091; G06F 16/35; G06F 11/3447; G06F 11/3452; G06F 16/258; G06F 16/735; G06F 17/10; G06F 17/15; G06F 17/18; C12Q 1/6886; C12Q 2600/106; C12Q 2600/112; C12Q 2600/156; C12Q 2600/158; C12Q 2537/143; C12Q 1/6809; C12Q 1/6883; C12Q 2537/159; C12Q 1/6827; C12Q 1/68; C12Q 2600/118; C12Q 2600/172; C12Q 2537/16; C12Q 2537/165; G16B 30/00; G16B 20/00; G16B 25/00; G16B 40/00; G16B 30/10; G16B 35/00; G16B 50/00; G16B 20/10; G16B 20/20; G16B 45/00; C12N 15/1093; C12N 15/1089; C12N 15/65; C40B 40/06; Y02A 90/24
See application file for complete search history.

(56) References Cited

U.S. PATENT DOCUMENTS

2016/0098519 A1* 4/2016 Zwir ............... G16B 20/00
702/19

OTHER PUBLICATIONS

Lu 2010 BMC Medical Genomics vol. 3:23 14 pages.*

(Continued)

*Primary Examiner* — Mary K Zeman
(74) *Attorney, Agent, or Firm* — Kilpatrick Townsend & Stockton LLP

(57) ABSTRACT

Cancer types (e.g., organ/tissue of origin and/or cancer subtype for an organ/tissue) can be distinguished by applying statistical methods to data samples consisting of counts of somatic single nucleotide variations (SNVs) across a tumor genome of a patient. For example, a factor loading matrix for each cancer type to be distinguished can be computed using a set of training data samples for which the cancer type is known. To determine the cancer type for a testing (or diagnostic) data sample, a regression analysis over the set of factor loading matrices yields statistical parameters that can be used to identify the cancer type.

25 Claims, 5 Drawing Sheets

Specification includes a Sequence Listing.

(56) References Cited

OTHER PUBLICATIONS

Ortiz-Estevez 2010 Bioinformatics 26, No. 15, pp. 1827 to 1833.*

Elhenawy 2012 IEEE GENSIPS Washington DC p. 82-85.*

Z.. Kakushadze. and W. Yu, 2016 "Factor Models for Cancer Signatures". Physica A pp. 462: pp. 527-559, 33 pages.

Z.. Kakushadze and W. Yu (2017) "*K-means and Cluster Models for Cancer Signatures". Biomolecular Detection and Quantification 13 (2017) pp. 7-31, 25 pages.

Z.. Kakushadze. and W. Yu. (2017) "Mutation Clusters from Cancer Exome". Genes 8(8): 201, 66 pages.

Wellcome Trust Sanger Institute. (2017) "Signatures of Mutational Processes in Human Cancer" (Cosmic), 7 pages.

S. Nik-Zainal et al., Breast Cancer Working Group of the International Cancer Genome Consortium. (2012) "Mutational Processes Molding the Genomes of 21 Breast Cancers". Cell 149(5): pp. 979-993, 15 pages.

L.B. Alexandrov, et al. (2013) "Deciphering Signatures of Mutational Processes Operative in Human Cancer", Cell Reports 3(1): pp. 246-259, 14 pages.

L.B. Alexandrov, et al.; (2013) "Signatures of Mutational Processes in Human Cancer". Nature 500 (7463): pp. 415-421, 11 pages.

T. Helleday, et al. (2014) "Mechanisms Underlying Mutational Signatures in Human Cancers". Nature Reviews Genetics 15(9): pp. 585-598, 14 pages.

L.B. Alexandrov and M.R. Stratton, (2014) "Mutational Signatures: the Patterns of Somatic Mutations Hidden in Cancer Genomes". Current Opinion in Genetics & Development. 24: pp. 52-60, 9 pages.

R.C. Grinold and R.N. Kahn, (2000) "A Quantitative Approach for Providing Superior Returns and Controlling Risk". Active Portfolio Management. (Second Edition) New York, NY: McGraw-Hill, 621 pages.

Z. Kakushadze, (2015) "Mean-Reversion and Optimization". Journal of Asset Management. 16(1): pp. 14-40, 27 pages.

Z. Kakushadze, (2015) "Heterotic Risk Models". Wilmott Magazine 2015(80): pp. 40-55, 16 pages.

Z. Kakushadze and W. Yu, (2016) "Multifactor Risk Models and Heterotic CAPM". The Journal of Investment Strategies 5(4): pp. 1-49, 50 pages.

Z Kakushadze and W. Yu, (2017) "Statistical Risk Models". The Journal of Investment Strategies 6(2): pp. 1-40, 40 pages.

M. Petljak and L.B. Alexandrov, (2016) "Understanding MutagenesisThrough Delineation of Mutational Signatures in Human Cancer". Carcinogenesis 37(6): pp. 531-540, 10 pages.

L.B. Alexandrov, et al. (2016) "Mutational Signatures Associated with Tobacco Smoking in Human Cancer". Science 354(6312): pp. 618-622, 6 pages.

M. Hollstein, et al. (2017) "Base Changes in Tumour DNA Have the Power to Reveal the Causes and Evolution of Cancer". Oncogene 36(2): pp. 158-167, 10 pages.

N.K. Hayward, et al. (2017) "Whole-genome Landscapes of Major Melanoma Subtypes". Nature 545(7653): pp. 175-192, 18 pages.

* cited by examiner

| Cancer Type | Granularity Level | Number of data samples | Number of correctly diagnosed data samples | Percentage of correctly diagnosed data samples |
|---|---|---|---|---|
| Bone Cancer | Organ | 57 | 35 | 61.40% |
| Breast Cancer | Organ | 686 | 428 | 62.39% |
| Chronic Lymphocytic Leukemia | Subtype | 152 | 134 | 88.16% |
| Chronic Myeloid Disorders | Organ | 46 | 45 | 97.83% |
| Colorectal Cancer | Organs Combined (Colon and Rectum) | 30 | 30 | 100.00% |
| Esophageal Adenocarcinoma and Gastric Cancer | Organs Combined (Esophagus and Stomach) | 296 | 261 | 88.18% |
| Liver Cancer | Organ | 377 | 338 | 89.66% |
| Leiomyosarcoma | Subtype | 67 | 52 | 77.61% |
| Lung Squamous Cell Carcinoma | Subtype | 30 | 29 | 96.67% |
| Malignant Lymphoma | Subtype | 241 | 189 | 78.42% |
| Skin Melanoma | Organ | 270 | 225 | 83.33% |
| Oral Cancer | Organ | 25 | 24 | 96.00% |
| Ovarian Cancer | Organ | 115 | 94 | 81.74% |
| Pancreatic Ductal Adenocarcinoma | Subtype | 416 | 285 | 68.51% |
| Pancreatic Endocrine Neoplasms | Subtype | 82 | 51 | 62.20% |
| Prostate Adenocarcinoma | Subtype | 407 | 295 | 72.48% |
| Kidney Renal Cell Cancer | Organ | 95 | 93 | 97.89% |

FIG. 5

SEQUENCE LISTING

```
<160> NUMBER OF SEQ ID NOS: 2

<210> SEQ ID NO 1
<211> LENGTH: 13
<212> TYPE: DNA
<213> ORGANISM: Unknown
<220> FEATURE:
<223> OTHER INFORMATION: Hypothetical sequence for illustrative purposes

<400> SEQUENCE: 1
agtgtgacct agt                                                          13

<210> SEQ ID NO 2
<211> LENGTH: 13
<212> TYPE: DNA
<213> ORGANISM: Unknown
<220> FEATURE:
<223> OTHER INFORMATION: Hypothetical sequence for illustrative purposes

<400> SEQUENCE: 2
agtgtgccct agt                                                          13
```

CANCER DIAGNOSTIC TOOL USING CANCER GENOMIC SIGNATURES TO DETERMINE CANCER TYPE

REFERENCE TO A "SEQUENCE LISTING" SUBMITTED AS ASCII TEXT FILES VIA EFS-WEB

The Sequence Listing written in file 102945-000100US-1057943_SequenceListing.txt created on Nov. 28, 2017, 715 bytes, machine format IBM-PC, MS-Windows operating system, in accordance with 37 C.F.R. §§ 1.821- to 1.825, is hereby incorporated by reference in its entirety for all purposes.

BACKGROUND

The present disclosure relates generally to cancer diagnostics and in particular to a diagnostic tool for determining a cancer type from DNA sequence data using a library of cancer genomic signatures.

Cancer is a disease resulting from uncontrolled and abnormal cell growth. It is currently understood that non-hereditary cancer results from somatic mutations in an individual's DNA. Different somatic mutations give rise to different types of cancer. Different types of cancer may be distinguished based on the organ or tissue of origin. In some cases, modern clinical and molecular pathology techniques support distinguishing multiple different subtypes of cancer affecting a given organ or tissue (e.g., hepatocellular carcinoma, intrahepatic bile duct carcinoma and hepatoblastoma are some of the currently known liver cancer subtypes). As used herein, the term "cancer type" may refer to a type of cancer (based on organ or tissue of origin) or a cancer subtype (for an organ or tissue). (Hereinafter, the term "organ" may refer to an organ or tissue, as applicable.) At present, the relationship between a particular somatic mutation and a particular cancer type is not well understood, although mutations in a few specific genes have been associated with particular cancer types.

Different types of cancer respond better to different treatment options. Thus, knowing the type of cancer a patient has is crucial to developing an optimal treatment plan. Further, cancer is a progressive disease, and early detection increases the prospects for successful treatment.

At present, the most common technique for detecting and diagnosing cancer begins with detecting a tumor, e.g., by tactile examination, visual inspection, and/or medical imaging. Once a tumor is detected, a biopsy can be performed. (As used herein, the term "biopsy" refers to a standard tumor biopsy where tissue or cell samples are taken.) During a biopsy, a medical professional extracts a tissue sample from the tumor area. This sample may be analyzed to determine whether it is cancerous and, if so, the type of cancer. A biopsy is typically an invasive and unpleasant procedure for a patient to endure, and like all invasive procedures, biopsy has medical risks. In addition, a biopsy is only useful after a tumor has become detectable; earlier detection may be desirable.

Currently, techniques are being developed to analyze cell-free DNA (cfDNA) extracted from a sample of a patient's blood in order to detect molecular abnormalities within the cfDNA population. A subpopulation of cfDNA with such abnormalities, referred to as circulating tumor DNA, or ctDNA, may be indicative of the presence of cancer in the tested patient. Such a procedure would be less invasive than a biopsy and may also support earlier detection of cancer. However, since blood circulates throughout the body, merely detecting indicia of cancer from a blood sample may not be sufficient information for developing a treatment plan. It is still necessary to identify the type of cancer, including the organ of origin. Thus, a blood test that merely indicates the patient has cancer would be of limited use. Further improvements are desirable.

SUMMARY

Certain embodiments of the present invention relate to diagnostic techniques that can be used to identify a cancer type based on analysis of somatic mutations in a patient's tumor DNA, which may be extracted from a blood sample or other tissue sample. (Depending on implementation, identifying the cancer type may include identifying the organ of origin and/or identifying a particular subtype of tumor for a given organ.)

The techniques described herein take as a starting point somatic mutations in a genomic tumor DNA sequence for a patient, which can be determined, e.g., by extracting cfDNA from a blood sample, sequencing the cfDNA, and obtaining somatic mutations from the ctDNA subpopulation, using existing (or future) techniques. From somatic mutations, single nucleotide variations, which are instances in the genomic sequence where one base has mutated to a different base, can be identified. As described below, each somatic single nucleotide variation (hereinafter referred to as "SNV," with the understanding that non-somatic single nucleotide variations can exist but are not of interest in the present context) can be categorized according to the base that was modified and the preceding and succeeding bases, resulting in a total of 96 categories of SNV.

It is assumed that different types of cancer have different patterns, or "cancer genomic signatures," of genomic SNVs. Accordingly, a cancer diagnostic tool can be developed based on statistical analysis of the genomic SNVs associated with different types of cancer. For instance, a training set of data samples can be obtained from patients whose cancer type has been determined using conventional techniques. (In some instances, the same patient may have more than one cancer type; each data sample is assumed to correspond to a single cancer type.) The training data set can include a number (N) of different cancer types, and for each cancer type i, there may be a number ($D_i$) of data samples. For each data sample, a 96-component vector representing the count of SNVs in each of the 96 categories of SNV is constructed. For each of the N cancer types, a 96×D, input matrix can be constructed by using the $D_i$ SNV count vectors as columns. A working matrix is defined from each input matrix by applying the same scaling function to each element of the input matrix, thus creating a set of N working matrices. In some embodiments, a logarithmic scaling function is applied to each element; other scaling functions may also be used (including a trivial scaling function for which a working matrix is the same as the corresponding input matrix).

Using the set of working matrices, a library of factor loading matrices (one matrix for each cancer type) can be constructed using statistical techniques similar to techniques that have been used in quantitative financial trading applications to assess portfolio risk. In one embodiment, each factor loading matrix is a 96×3 matrix, where a first column is determined by computing a 96-component vector σ[i] whose components are the mean values for the rows of the corresponding working matrix for the cancer type i; a second column is determined by computing a 96-component vector σ[i] whose components are the standard deviations for the rows of the corresponding working matrix for the cancer type i; and a third column, which is common to all cancer types, whose components are determined by computing an intermediate vector $B[i]=\mu[i]/\sigma[i]$ for each cancer type i, arranging the N intermediate vectors $B[i]$ into a 96×N intermediate matrix, and computing row means of the intermediate matrix, with the vector of row means being used as the third column. In other embodiments, some or all of the factor loading matrices may include fewer than these three columns, and in still other embodiments, some or all of the factor loading matrices may include additional columns (e.g., based on principal component analysis as described below). If desired, the factor loading matrices for different cancer types may have different numbers of columns.

Once the library of factor loading matrices has been constructed, it can be used to diagnose cancer type in a test data sample. For example, the 96 SNV counts for the test data sample can be determined, e.g., using conventional (or future) techniques. A 96-component working vector can be defined, where each component of the working vector is defined by applying to the corresponding SNV count the same scaling function that was used to define the working matrices for the training data, e.g., a logarithmic scaling function. For each cancer type, a regression analysis is run of the working vector over the corresponding factor loading matrix, and the corresponding regression residual vector is determined. Based on the residual vectors, cancer type can be diagnosed. For example, in some embodiments, the 96 SNV categories can be grouped into six independent channels (with 16 SNV categories in each channel) according to which base mutation occurred. Using this channel grouping, additional statistical analysis can be performed on the working vector and the regression residual vector to determine the cancer type.

Specific examples of analysis processes are described below.

The following detailed description, together with the accompanying drawings, will provide a further understanding of the nature and advantages of the claimed invention.

BRIEF DESCRIPTION OF THE DRAWINGS

FIG. 5 shows a table with representative results from an analysis performed according to an embodiment of the present invention.

DETAILED DESCRIPTION

Certain embodiments of the present invention relate to diagnostic techniques that can be used to identify a cancer type based on analysis of somatic mutations in a patient's tumor DNA, which may be extracted from a blood sample or other tissue sample. Depending on implementation, identifying the cancer type may include identifying the organ of origin and/or identifying a particular subtype of tumor for a given organ.

The techniques described herein take as a starting point somatic mutations in a complete genomic sequence of tumor DNA for a patient, which can be determined, e.g., from a blood sample using existing (or future) techniques. Examples include Whole Genome Sequencing (WGS) and Whole Exome Sequencing (WES). (WES is a targeted DNA sequencing of the protein-encoding regions of a genome; WES data may be useful for cancer types with high SNV counts such as cancers with hypermutator characteristics; for many tumors WES data is sparsely populated with many null SNV counts in the corresponding input data matrix; for such tumors WGS data can be used.) Other sequencing techniques may also be used, provided that the result is a complete (or essentially complete) genomic sequence that allows identification of single nucleotide variations in somatic mutations. (It should be noted that in practice, in techniques such as WGS and WES, sequencing is not exactly complete; however, it is essentially complete and allows identification of single nucleotide variations in somatic mutations.)

Figure 1A:
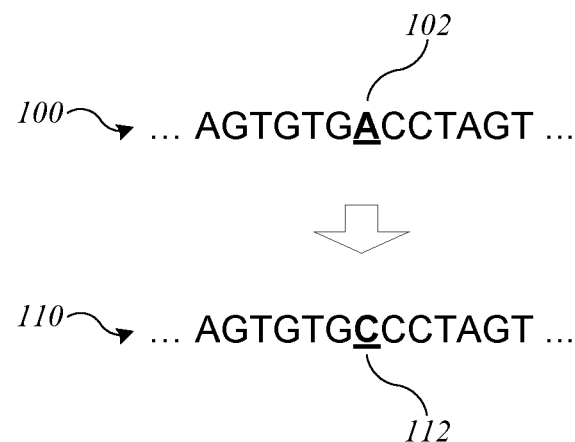
FIG. 1A shows an example of a somatic single nucleotide variation (SNV) in a DNA sequence (SEQ ID NOS:1-2, respectively).

As used herein, a "somatic single nucleotide variation" (SNV) refers to a mutation that occurs only in a single base at a specific location in a patient's genomic tumor DNA sequence and that is not present in the same specific location in the patient's genomic normal DNA sequence. (The standard notation of A, C, G, T, is used herein to denote the bases adenine, cytosine, guanine, and thymine.) An example is shown in FIG. 1A. Sequence 100 (representing a small part of a genomic DNA sequence) includes an instance 102 of base A, while sequence 110 substitutes an instance 112 of base C at the corresponding position; the bases on either side of the mutated base are the same in sequences 100 and 110. Since DNA has four bases, there are twelve possible single-base mutations. For purposes of the techniques described herein, it is useful to distinguish six independent base mutations; the other six are considered equivalent due to base complementarity (whereby A in one strand of the DNA's double helix always binds with T in the other strand, and C always binds with G). For example, the six independent base mutations can be identified as C>A, C>G, C>T, T>A, T>C, T>G, where the notation "X>Y" means "base X mutates into base Y"; the other six base mutations G>T, G>C, G>A, A>T, A>G, A>C are considered equivalent to the first six base mutations due to base complementarity.

Figure 1B:
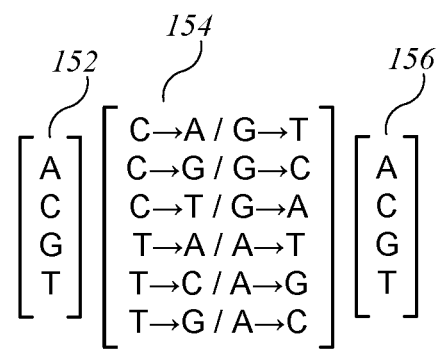
FIG. 1B schematically illustrates a set of possible SNVs that can be used in some embodiments of the present invention.

For each of the six distinct mutations, any of the four bases can immediately precede or succeed the mutated base. FIG. 1B schematically illustrates a set of categories of SNV that can be used in some embodiments of the present invention. Position 154 is occupied by one of the six distinct mutations. Preceding position 152 can be occupied by any of the four bases, and succeeding position 156 can also be occupied by any of the four bases. Accordingly, for present purposes, 96 (4×6×4) categories of SNV can be distinguished.

It is assumed that different types of cancer have different patterns, or cancer genomic signatures, of SNVs across the cancer genome. Accordingly, a cancer diagnostic tool can be developed based on statistical analysis of the SNVs in cancer genomes associated with different types of cancer. For instance, a large set of data samples from patients whose cancer type has been determined using conventional techniques can be used as a training data set to determine statistical signatures associated with different cancer types.

These statistical signatures can be used to evaluate data samples from other patients whose cancer type may be unknown.

Figure 2:
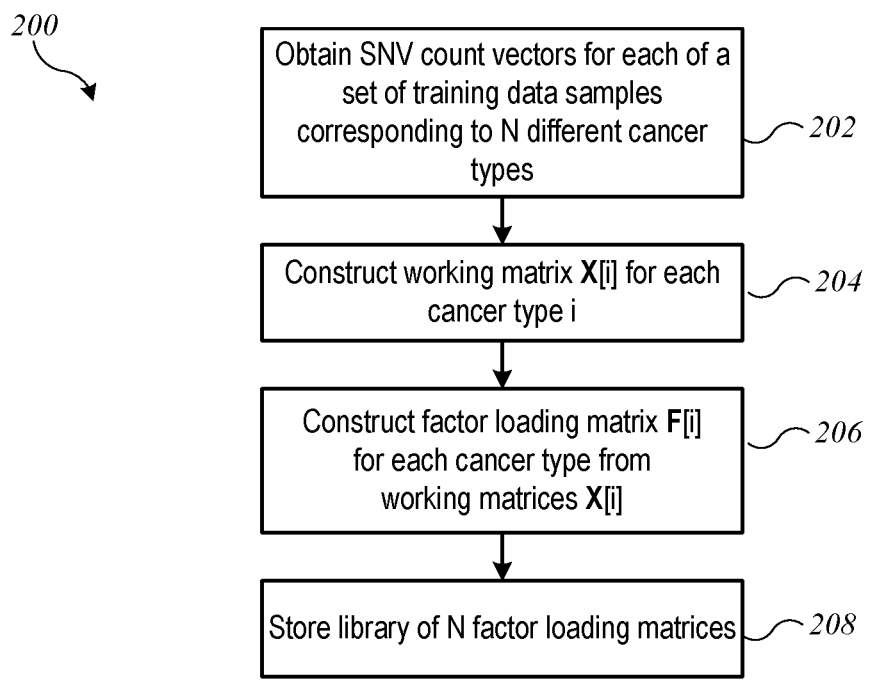
FIG. 2 is a flow diagram of a training process according to an embodiment of the present invention.

FIG. 2 is a flow diagram of a training process 200 according to an embodiment of the present invention. At block 202, SNV count vectors are obtained for each of a set of training data samples corresponding to N different cancer types. Each training data sample can include somatic mutations based on, e.g., WGS data obtained for a patient with a cancer type that has been determined, e.g., using conventional techniques such as biopsies. For example, to obtain a training data sample, a tumor tissue sample can be obtained from a patient, tumor DNA can be sequenced, and somatic mutations can be identified. It is assumed that a sufficiently large number of training data samples are available (so that cancer genomic signatures generated from the training data samples are statistically significant) and that each training data sample is associated with one or another of a set of N different cancer types that it is desirable to distinguish. As noted above, "cancer type" may include the organ of origin and/or a specific subtype of cancer that afflicts a given organ. In some instances, it may be sufficient to identify the organ of origin. In other instances, it may be desirable to distinguish among different cancer subtypes originating in the same organ. "Mixed" cases are also contemplated where the set of cancer types has organ-level granularity and further distinguishes among at least some of the subtypes for at least some organs. In general, it is assumed that there are N different cancer types to be distinguished and that, for each cancer type i, the training data set includes a number ($D_i$) of training data samples. The number $D_i$ can be the same or different for different cancer types. Since the analysis is based on statistical properties, larger values of $D_i$ are generally preferred, limited only by available data samples and processing power. In one example, a training data set includes 3,392 data samples (genomic tumor DNA sequences determined using WGS) representing 17 cancer types; those skilled in the art will appreciate that any number of data samples and any number of cancer types can be used. That said, embodiments of the present invention use statistical analysis to identify cancer genomic signatures, and a training data set that contains too few data samples for a given cancer type may not produce statistically significant cancer genomic signatures.

The SNV count vector for a training data sample can be determined by counting the number of occurrences of each of the 96 categories of SNV across the entire cancer genome. Conventional techniques for identifying SNVs from genomic tumor DNA sequence data may be applied. It should be noted that the counting of SNVs can be carried out across the entire cancer genome rather than being restricted to specific genes (e.g., genes believed to be associated with particular types of cancer).

At block 204, a "working matrix" X[i] is constructed for each of the N cancer types. For example, the SNV count vectors for the $D_i$ training data samples of the ith cancer type can be arranged as the columns of a 96×$D_i$ matrix G[i]. (It should be noted that the matrix G[i] is not symmetrical.) The elements of matrix G[i] are, by definition, non-negative integers. Further, because the elements are counts, they may be expected to have, e.g., skewed distributions that are roughly, albeit not exactly, log-normal. Accordingly, in some embodiments it is useful to work with logarithmic count values. For example, if $g[i]_{ab}$ is an element of matrix G[i], then the corresponding element $x[i]_{ab}$ of working matrix X[i] can be defined as:

$$x[i]_{ab} = \ln(g[i]_{ab} + 1). \tag{1}$$

It should be noted that each element $x[i]_{ab}$ is also non-negative. As noted below, other scaling functions can be used, including a trivial scaling function for which $x[i]_{ab} = g[i]_{ab}$.

At block 206, a library of factor loading matrices (also sometimes referred to as factor loadings matrices) F[i]—one matrix per cancer type—can be constructed from the working matrices X[i]. Construction of the factor loading matrices (FLMs) can rely on statistical (or other) techniques similar to techniques that have been used in quantitative financial trading applications to assess portfolio risk. Each FLM F[i] can be a 96×$C_i$ matrix, where $C_i$ is a number of columns, and each column can be determined using a different statistical computation. $C_i$ can be, e.g., 1, 2, 3, or a larger number. In some embodiments, the FLMs for different cancer types i can have different numbers of columns. It should be noted that factor loading matrices are example embodiments of cancer genomic signatures.

Examples of statistical quantities that can be used to populate columns of the FLMs F[i] will now be described. It is assumed that the person skilled in the art will be familiar with standard statistical computations (e.g., mean, standard deviation, correlation matrix, principal components, regression, etc.), and specific algorithms or formulas for such computations have been omitted.

(1) Row Means.

The mean of each row of the working matrix X[i] can be separately computed, forming a 96-element vector μ[i] for each cancer type i. The vector μ[i] may be used as a column of the FLM F[i].

(2) Row Standard Deviations.

The standard deviation of each row of the working matrix X[i] can be separately computed, forming a 96-element vector σ[i] for each cancer type i. The vector σ[i] may be used as a column of the FLM F[i].

(3) Global Mean-to-Standard-Deviation Ratio.

After computing the mean and standard deviation of each row of the working matrix for cancer type i, a 96-element intermediate vector B[i] can be defined as $$B[i] = \mu[i]/\sigma[i] \tag{2}$$

A 96×N intermediate matrix B3 can be formed using the N vectors B[i] as columns. Then row means of intermediate matrix B3 can be computed, forming a 96-element vector β3, which can be used as a column in the FLM F[i] for each cancer type. It should be noted that vector β3 is the same for all cancer types.

(4) Global Mean-to-Variance Ratio.

Instead of the global mean-to-standard-deviation ratio, other variants of such ratios can be constructed. For example, after computing the mean and standard deviation of each row of the working matrix for cancer type i, a 96-element variance vector v[i] can be defined as a square of the 96-element standard deviation vector σ[i], and a 96-element intermediate vector B1[i] can be defined as $$B1[i] = \mu[i]/v[i] \tag{2}$$

A 96×N intermediate matrix B4 can be formed using the N vectors B1[i] as columns. Then row means of intermediate matrix B4 can be computed, forming a 96-element vector β4, which can be used as a column in the FLM F[i] for each cancer type (e.g., together with or instead of β3). It should be noted that vector β4 is the same for all cancer types. Those skilled in the art will appreciate that other columns in the FLMs can be constructed.

(5) Non-Type-Specific Principal Components.

Using the 96×N matrix B3, a 96×96 covariance matrix C1 can be computed (by rows) using standard techniques. Principal components {Q1[1], Q1[2], ... } of the matrix C1 can be computed, again using standard techniques. The principal components can be ordered based on decreasing eigenvalues (Q1[1] corresponds to the largest eigenvalue, Q1[2] to the next largest, etc.), and one or more of these principal components can be used as columns of the FLM F[i] for each cancer type. Since B3 is the same for all cancer types, principal component columns computed in this manner will also be the same for all cancer types. It is also noted that including zero or just the first principal component (i.e., just Q1[1] corresponding to the largest eigenvalue) in the FLM may be preferred, as higher-order principal components (i.e., those corresponding to eigenvalues other than the largest eigenvalue) can be unstable. Other variations on this analysis may also be employed. For example, the correlation matrix can be used instead of the covariance matrix as C1. Another variation includes computing a regression of B[i] over the 96-element vector β3, with or without the intercept; forming a 96×N intermediate matrix using as columns the N 96-element vectors corresponding to the regression residuals; computing the 96×96 covariance matrix (or correlation matrix if desired) from this intermediate matrix of residuals; then using one or more principal components of this 96×96 covariance or correlation matrix as columns of each of the FLMs F[i].

(6) Type-Specific Principal Components.

Using the 96×$D_i$ working matrix X[i] for cancer type i, a 96×96 covariance matrix C2[i] can be computed (by rows) using standard techniques. Principal components {Q2[i][i], Q2[i][2], etc.} of the matrix C2[i] can be computed, again using standard techniques. The principal components can be ordered based on decreasing eigenvalues, and one or more of these principal components can be used as columns of the FLM F[i] for cancer type i. In this example, the principal components for different cancer types will generally not be the same. As in the non-type-specific example, including zero or just the first principal component (i.e., just Q2[i][i] corresponding to the largest eigenvalue of C2[i]) in the FLM F[i] may be preferred, as higher-order principal components (i.e., those corresponding to eigenvalues other than the largest eigenvalue) can be unstable. Other variations on this analysis may also be employed. For example, the correlation matrix can be used instead of the covariance matrix as C2[i]. Another variation includes, for each cancer type i, computing a regression of each of the N columns of X[i] over a matrix whose columns include at least some of the columns described above (e.g., β[i], σ[i], β3 and/or Q1[1]), with or without the intercept; forming a 96×N intermediate matrix using as columns the N 96-element vectors corresponding to the regression residuals; computing the 96×96 covariance matrix (or correlation matrix if desired) from this intermediate matrix of residuals; then using one or more principal components of this 96×96 covariance or correlation matrix as columns of the FLM F[i].

In various embodiments, a given FLM F[i] can include any or all of these columns. (It will be appreciated that an FLM F[i] cannot have more than 96 linearly independent columns; in practice some columns may not be exactly collinear but nearly collinear thereby adding little to no value; further, including in the FLM F[i] new linearly independent columns may not always add value.) For example, in one embodiment, each FLM F[i] includes p[i] as a first column, σ[i] as a second column, and β3 as a third column. In another embodiment, each FLM F[i] includes these three columns and one or more columns for principal components (Q1[1] and/or Q2[i][1], etc.). The number of columns in F[i] for different cancer types i can be the same or different, and the selection can be optimized, e.g., by comparing performance of the testing process described below for FLMs constructed using different combinations of columns.

At block 208, a library consisting of the NFLMs F[i] can be stored, and training process 200 can end. The FLMs can be used in a cancer diagnostic process as described below.

It will be appreciated that process 200 is illustrative, and variations and modifications are possible. The number of cancer types and number of training data samples can be varied as desired and may be based on what data is available at any given point in time. The particular combination (and order) of columns in the FLMs can be varied, and (as noted above) the FLMs for different cancer types can have different numbers and/or combinations of columns. Other columns may be defined using any statistical quantity that can be computed deterministically from the working matrices X[i]. At least some of the columns in a given FLM should be dependent on cancer type, so that FLMs for different cancer types can be expected to not be identical. (If the FLMs for different cancer types are identical, the diagnostic process described below will not be able to distinguish among those cancer types.) It will be appreciated that inclusion of non-type-specific columns in the FLM F[i] (i.e., columns that are the same for all cancer types i) can serve the purpose of identifying and factoring out common factors (i.e., "noise" not specific to each cancer type) in the diagnostic process described below, so that the contributions of the type-specific factors can be amplified.

In some embodiments, a portion of the training data may be reserved for use as testing data to evaluate the result of process 200, and iterative testing and adjusting of the definitions of the FLMs can be performed to improve the quality of results (e.g., the fraction of cases in which the cancer type is correctly identified).

It should be noted that process 200 involves deterministic statistical analysis and does not rely on nondeterministic machine-learning techniques. This reduces the computational power required for training. Further, the FLMs are based on statistical computations that are understood as reflecting properties of the underlying data; unlike the end products of a typical (nondeterministic) machine-learning algorithm, the FLMs are not simply a black box to humans. It is also noted that (nondeterministic) machine-learning algorithms generally struggle with extracting a signal from noisy data sets; quantitative analysis techniques of the type described herein may be better suited to the task.

Figure 3:
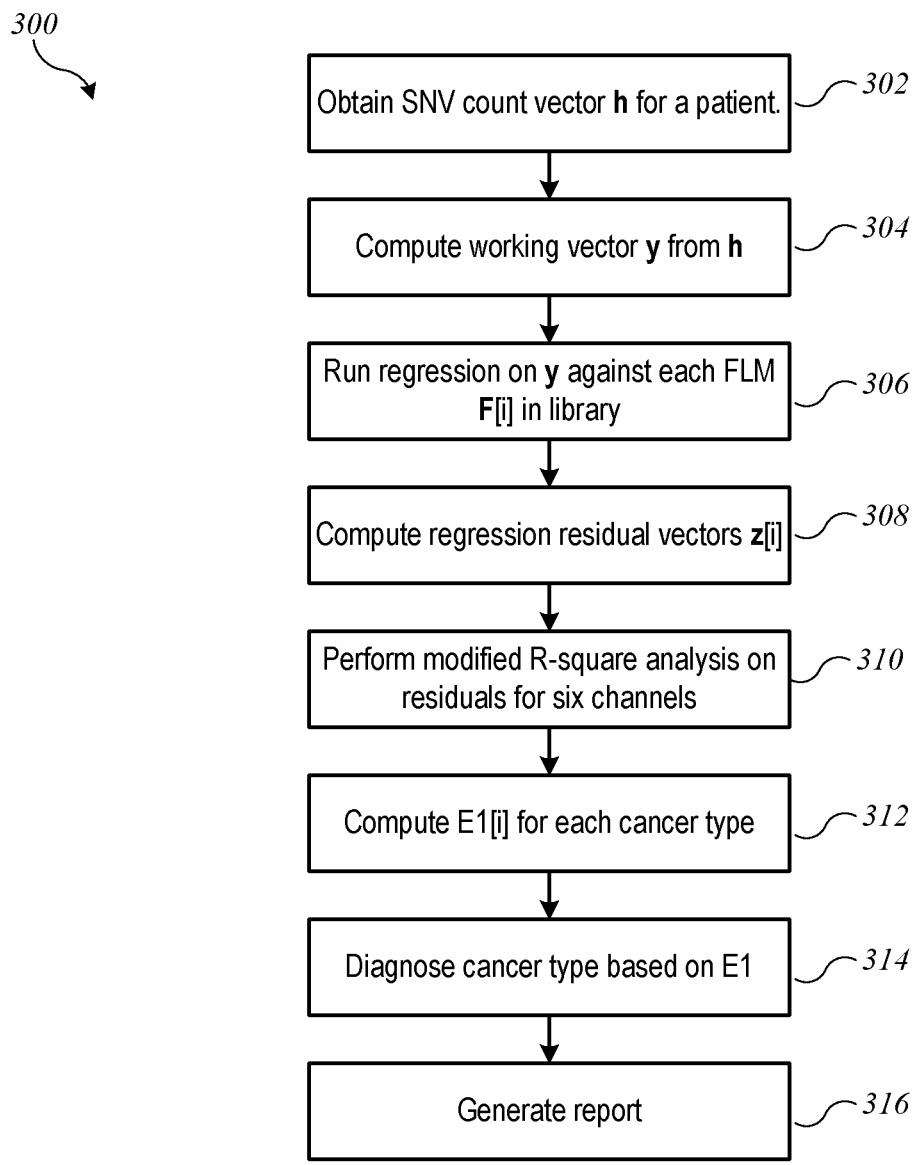
FIG. 3 is a flow diagram of a diagnostic process according to an embodiment of the present invention.

Once the library of factor loading matrices F[i] has been constructed, it can be used to diagnose cancer type in a test data sample, which may include genomic tumor DNA sequence data from a patient who has cancer of an unknown type. FIG. 3 is a flow diagram of a diagnostic process 300 according to an embodiment of the present invention.

At block 302, a test data sample including a 96-component SNV count vector h is obtained. The same techniques used to obtain the SNV count vectors for the training data samples can be used. It should be noted that the tumor DNA extraction and/or sequencing techniques used to provide data for the training and diagnostic processes need not be the same, as long as a complete (or essentially complete) genomic sequence is available in a format such that SNVs can be counted. (As noted above, for some tumors with high SNV counts due to hypermutation characteristics WES data may be useful. Such WES data samples can be useful as training data samples. For test data samples, the cancer type a priori is unknown and a WES test data sample may turn out to be too sparsely populated to be useful, in which case a WGS test data sample can be obtained.)

At block 304, a working vector y is computed from SNV count vector h by applying a scaling function. For example, if $h_a$ is a component of vector h, then the corresponding component)), of working vector y can be defined as:

$$y_a = \ln(h_a + 1), \tag{3}$$

similarly to block 204 of process 200 described above. As with process 200, other scaling functions can be used, provided that the scaling function used at block 304 is the same one that was used at block 204 of process 200.

At block 306, for each of the N cancer types i represented by the FLMs F[i] in the library, a regression of working vector y against F[i], with the intercept, is run. At block 308, for each cancer type, a regression residual is computed as a 96-component vector z[i].

At block 310, a modified R-squared analysis is performed on the regression residuals z[i]. Specifically, for purposes of this analysis, the 96 SNV categories illustrated in FIG. 1B can be grouped into six channels, where each channel corresponds to one of the six distinct base mutations (at position 154) and includes all 16 of the 96 SNV categories having the channel-defining mutation. For each channel j, a 16-component vector yc[j] is defined by restricting the 96-component working vector y to the components corresponding to channel j. The mean y1[j] is computed by taking the average of the 16 components yc[j]k of yc[j]. A sum of squares of deviations for yc[j], referred to as y2[j], can be computed by summing the quantity $(yc[j]k - y1[j])^2$ over the 16 components yc[j]k of vector yc[j].

Similarly, for each channel j, a 16-component vector zc[i, j] is defined by restricting the 96-component residual vector z[i] to channel j. The sum of squares for zc[i, j], referred to as z2[i, j] can be computed by summing the quantity $(zc[i, j]k)^2$ over the 16 components $zc[i, j]_k$ of vector zc[i, j]. The following modified R-squared parameter E[i,j] is computed:

$$E[i,j] = 1 - z2[i,j]/y2[j]. \tag{4}$$

E[i, j] is similar to a standard regression R-squared parameter, except that the regression in this case is performed using the 96-component vector y while E[i, j] is computed for the 16 components in each of the six channels j.

At block 312, for each cancer type i, a composite parameter E1[i] is computed by averaging E[i, j] over the six channels j. This averaging can be done with uniform weights, which, for each cancer type i, amounts to summing E[i, j] over the six channels j and dividing by 6. Such averaging can also be done with nonuniform weights which can be optimized to improve the quality of results (e.g., the fraction of cases in which the cancer type is correctly identified). It should be noted that such nonuniform weights may not always be out-of-sample stable (i.e., stable from one training data set to another nonoverlapping training data set) and using uniform weights may be preferred.

At block 314, cancer type can be diagnosed based on the E1[i] values. For example, the cancer type can be diagnosed as the cancer type i that produced the largest E1[i]. It will be appreciated that basing the diagnosis on E1[i] instead of directly on, e.g., working matrices X[i] is advantageous as the latter contain much noise which is largely filtered out of E1[i].

At block 316, a diagnostic report can be generated. The diagnostic report can include results obtained during execution of process 300, such as the diagnosed cancer type, the likelihood of the diagnosed cancer type and/or confidence level, the E1[i] value for each cancer type, and/or values of various quantities computed during earlier stages of the analysis process. In various embodiments, results can be presented in graphical, numerical, and/or text-based formats. The diagnostic report can be delivered to an end user, e.g., the person (such as an oncologist) or entity (such as a laboratory) that requested testing of the patient data sample.

It will be appreciated that process 300 is illustrative and that variations and modifications are possible. In some embodiments, process 300 can be used to test the accuracy of the described technique by executing process 300 on testing data for which the cancer type has been determined using other techniques such as biopsies. Based on the results, the definition of, e.g., the FLMs F[i] and/or the composite parameters E1[i] can be refined to improve the accuracy.

It should also be noted that diagnosing the cancer type based on the largest value of E1[i] is only one out of a number of possibilities, and variations and modifications are possible. Thus, other methods can be employed, such as analyzing all N composite parameters E1[i].

For instance, one analysis can be based on comparing the N-component vector E1, whose components are E1[i], for the test data sample to such vectors for each of the training data samples. For each cancer type i, each column of the working matrix X[i] is a 96-component vector. The number of such vectors is D. The total number M of such 96-component vectors across all cancer types is the sum of $D_i$ over the N values of i. For each such 96-component vector Y[c] (where c takes M values) a composite parameter L1[c][i] can be computed in the same manner as the composite parameter E1[i] is computed for the working vector y for the test data sample. (The computation of L1[c][i] involves, for each cancer type i, regressing 96-component vector Y[c] over the FLM F[i], computing the modified R-squared parameters L[c][i, j] from the regression residual vectors in the same manner as the modified R-squared parameters E[i, j] are computed from the residual vectors in the regression of y over the FLM F[i], and then averaging L[c][i, j] over the six channels j. As above, this averaging can be performed with uniform or nonuniform weights.)

For each value of c, the N parameters L1[c][i] can be combined into an N-component vector L1[c]. (There are M such N-component vectors.) For some preset integer K, which can take values 1, 2, 3, or a larger value (the value of K can be optimized to improve accuracy), K nearest neighbors of the vector E1 can be identified among the M vectors L1[c]. (For each value of c, the distance between two N-component vectors E1 and L1[c] can be defined using one of the standard definitions. E.g., Euclidean distance d[c] can be defined as the square root of the sum of $(E1[i] - L1[c][i])^2$ over the N values of i. Those skilled in the art will appreciate that other definitions of the distance can be used, e.g., Manhattan distance, cosine distance, etc.)

The cancer type corresponding to each vector L1[c] is known as each such vector corresponds to a training data sample. The number S[i] of vectors L1[c] with cancer type i present among the K nearest neighbors of the vector E1 can be counted. The cancer type for the test data sample then can be diagnosed as that with the largest such count S[i]. It should be noted that ties can arise as there can be more than one cancer types with the largest count.

In some embodiments, ties can be avoided by modifying the definition of S[i]. For example, for N preset parameters p[i], each with a value greater than 0 and smaller than 1, S[i]

can be defined as a weighted count as follows. First, the vectors L1[c] can be ordered such that the distance d[c] is increasing. Next, only the first K vectors L1[m] are kept (so m takes K values), which correspond to the K nearest neighbors of E1. For a given value of i, K contributions S[i, m] can be defined as equal to x) p[i] to the power (m−1) if the cancer type of L1[m] is i, and y) 0 if the cancer type of L1[m] is not i. (It should be noted that, with this definition, S[i, 1] is equal to 1 if the cancer type of L1[m] is i, and S[i, 1] is equal to 0 if the cancer type of L1[m] is not i.) Then, for each cancer type i, modified parameter S[i] can be defined by summing contributions S[i, m] over the K values of m. The cancer type for the test data sample then can be diagnosed as that with the largest value of S[i]. (It should be noted that parameters p[i] can have the same or different values for different cancer types and, e.g., these parameters can be optimized to improve accuracy.)

A hybrid of the two methods described above (one based on the maximum value of E1[i], and the other one based on the K nearest neighbors of E1 among the vectors L1[c]) for diagnosing the cancer type for a test data sample can also be considered. Tentative cancer type it can be defined as the cancer type i that produces the largest E1[i]. For a given value of i, K contributions S[i, m] can be defined as equal to x) p[i] to the power m if the cancer type of L1[m] is i, and y) 0 if the cancer type of L1[m] is not i. For each cancer type i, intermediate parameter S1[i] can be defined by summing S[i, m] over the K values of m. For each cancer type i, modified parameter S[i] can be defined as equal to x) S1[i]+1 if i equals i1, and y) S1[i] if i does not equal i1. The cancer type for the test data sample then can be diagnosed as that with the largest value of S[i]. Those skilled in the art will appreciate that other variations and modifications are possible.

In some embodiments, other statistical quantities can be used. For instance, in the examples described above, the statistical analysis is based on a logarithm of the SNV counts. In some embodiments, a second analysis can be performed using a different scaling function. For example, during training, a second working matrix XX[i] can be defined using a scaling function different from that used in the definition of the first working matrix X[i]. One example uses a "double-log" matrix where, for each cancer type i, the elements of the matrix XX[i] can be defined as $xx[i]_{ab}=\ln (x[i]_{ab}+1)=\ln (\ln (g[i]_{ab}+1)+1)$, and the N matrices XX[i] can be used to generate a second set of FLMs FF[i]. For diagnosis, a double-log vector yy can be defined for the test data sample such that its elements are defined as $yy_a=\ln+1)=\ln (\ln (h_a+1)+1)$, and the analysis of process 300 can be repeated for the double-log vector yy to generate a second composite parameter EE1[i] (computed using yy and FF[i]) in the same manner as described above for computing the composite parameter E1[i] (using y and F[i]) for each cancer type. Cancer type can be diagnosed based solely on EE1[i] (e.g., the cancer type that yields the largest EE1[1]) or on a combination of both the single-log and double-log analyses, e.g., the cancer type that yields the largest sum of E1+EE1[1] is the cancer type the patient is diagnosed as having.

Other scaling functions of the SNV counts can also be used (e.g., square or some other power of $g[i]_{ab}$, square root or some other fractional power of $g[i]_{ab}$, square or some other power of $x[i]_{ab}$, square root or some other fractional power of $x[i]_{ab}$, and so on), and any number of analyses using any number of different scaling functions can be combined, e.g., by adding (similarly to the above example involving two composite parameters E1[i] and EE1[1]) the composite parameters corresponding to each such scaling function for each cancer type i, either with uniform weighs (as in the above example involving two composite parameters E1[i] and EE1[1]), or with nonuniform weights which can be optimized to improve accuracy. Also, similarly to the example described above for the composite parameter E1[i], for a combination of composite parameters corresponding to different scaling functions the cancer type can be diagnosed based on the maximum value thereof, or using the method based on nearest neighbors, or a hybrid of these two methods, and so on.

Figure 4:
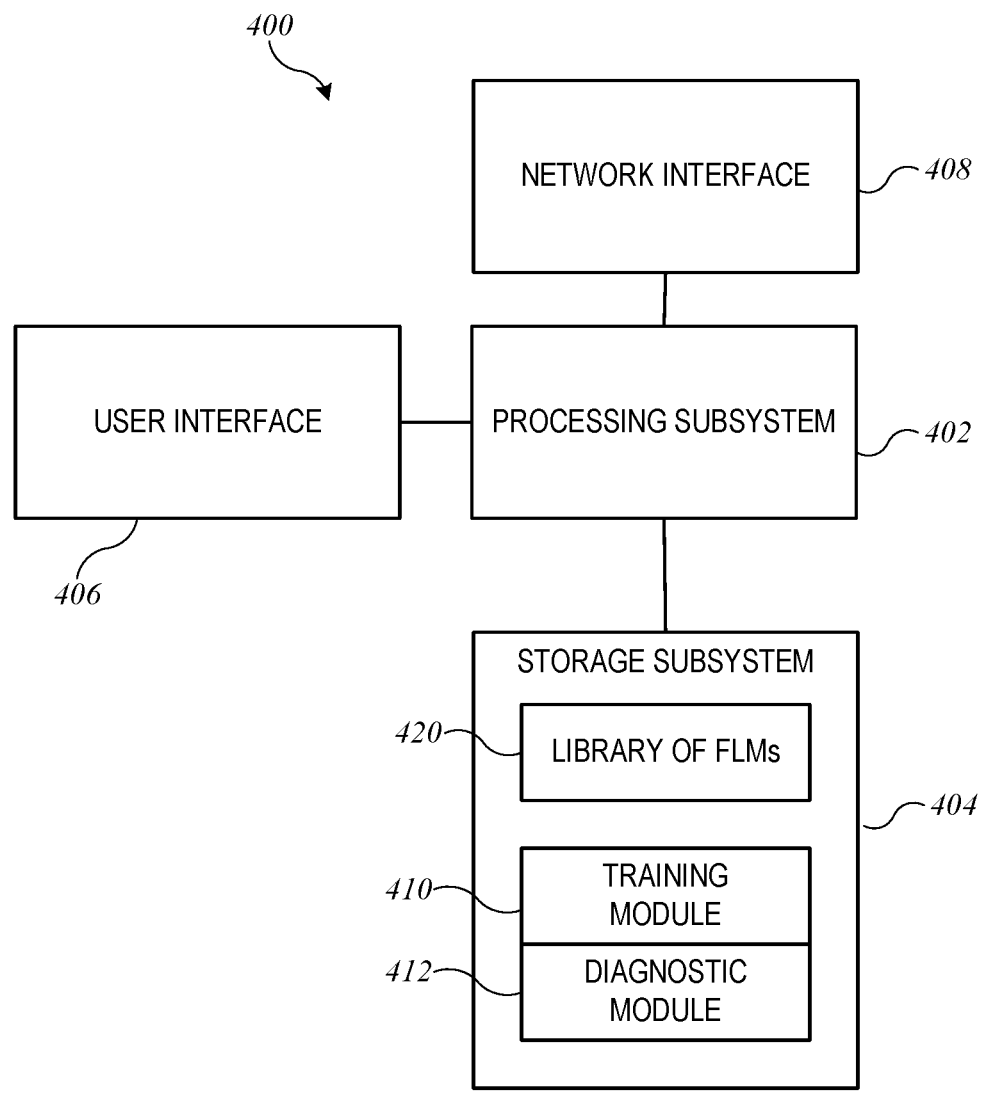
FIG. 4 is a simplified block diagram of a computer system implementing an embodiment of the present invention.

The training and diagnostic processes described herein can be implemented using computer systems of generally conventional design, programmed to carry out operations of processes 200 and 300 or similar processes. FIG. 4 is a simplified block diagram of a computer system 400 implementing an embodiment of the present invention. In this implementation, computer system 400 includes processing subsystem 402, storage subsystem 404, user interface 406, and network interface 408.

Processing subsystem 402 can include one or more general purpose programmable processors capable of executing program code instructions to perform various operations, including operations described therein. In some embodiments, processing subsystem 402 may incorporate scalable processing hardware (e.g., an array of server blades or the like) that can be adapted dynamically to varying processing needs.

Storage subsystem 404 can include a combination of volatile and nonvolatile storage elements (e.g., DRAM, SRAM, flash memory, magnetic disk, optical disk, etc.). Portions of storage subsystem 404 may be used to store program code to be executed by processing subsystem 404. Examples of program code can include training module 410 (e.g., code implementing process 200 of FIG. 2) and diagnostic module 412 (e.g., code implementing process 300 of FIG. 3). Portions of storage subsystem 404 may also be used to store a library 420 of factor loading matrices generated, e.g., using process 200.

User interface 406 can include user input devices and/or user output devices. Examples of user input devices include a keyboard, mouse, joystick, touch pad, touch screen, microphone, and so on. Examples of user output devices include a display device (which may be touch-sensitive), speakers, indicator lights, a printer, and so on.

Network interface 408 can be implemented using any combination of hardware and software components that together enable communication with other computer systems. In some embodiments, network interface 408 may communicate with a local area network (LAN) using Ethernet, Wi-Fi, or other similar technologies, and the LAN may enable communication with a wide area network (WAN) such as the internet. Via network interface 408, computer system 400 can communicate with one or more other computer systems to support distributed implementations of processes described herein. For example, in some embodiments, generation of a library of factor loading matrices (e.g., using process 200 described above) can be performed on one instance of computer system 400 (or a group of computer systems such as a server farm), and the resulting library can be distributed to one or more other instances of computer system 400 for use in a diagnostic process (e.g., process 300 described above). As another example, a training data set may be housed on a server that can be accessed by computer system 400 via network interface 408.

In some embodiments, computer system 400 may operate in a server configuration, communicating with one or more client computers via network interface 408. For example, medical professionals operating client computers may submit requests for diagnosis (e.g., including genomic tumor DNA sequence data) to computer system 400 via network interface 408. Computer system 400 may execute diagnostic module 412 and return a report to the client computer via network interface 408. In embodiments where computer system 400 is operated remotely via network interface 408, local user interface 406 may be limited (e.g., just a few indicator lights) or omitted entirely. The entire diagnostic process can be automated if desired.

It will be appreciated that computer system 400 is illustrative and that variations and modifications are possible. For instance, although computer system 400 and its operations are described herein with reference to particular blocks, it is to be understood that these blocks are defined for convenience of description and are not intended to imply a particular physical arrangement of component parts or a particular software architecture. Further, the blocks need not correspond to physically distinct components. Blocks can be configured to perform various operations, e.g., by programming a processor or providing appropriate control circuitry, and various blocks might or might not be reconfigurable depending on how the initial configuration is obtained. Embodiments of the present invention can be realized in a variety of apparatus including computing devices and computer systems implemented using any combination of circuitry and software.

A diagnostic tool of the kind described herein has been implemented and tested, for purposes of demonstrating efficacy. Somatic mutation data was downloaded from the open data release 25 of the International Cancer Genome Consortium (ICGC) (available for anonymous download via the ICGC Data Portal at https://dcc.icgc.org/releases/release_25/Projects/). Using this data, SNV count matrices G[i] were generated for each cancer type i in the manner described above. Specifically, for each cancer type, the data was filtered for somatic single nucleotide variations (SNVs). The data was further subset into two groups based on whether the data was generated using whole-genome sequencing (WGS) or whole-exome sequencing (WES). For both WGS and WES subsets, a unique data sample identification hash was generated for each data sample (which, in a small fraction of cases, includes accounting for the existence of multiple data samples originating from a single donor, e.g., when a donor has multiple different cancer types). In some cases the data contains multiple entries for the same somatic mutation (e.g., due to ICGC's policy of including multiple entries to account for a single genomic mutation annotating to multiple gene transcripts, or inclusion of entries corresponding to multiple variant caller algorithms). All such duplicated entries were identified and reduced to a single entry to avoid SNV overcounting. Then, for each data sample, SNVs were counted and grouped into a 96-element vector of SNV counts according to the 96 categories of SNV (defined above), and, for each cancer type i, 96×$D_i$ input matrix G[i] was constructed by using the $D_i$ SNV count vectors (for the $D_i$ data samples with the cancer type i) as columns.

For purposes of this analysis, only WGS data was used. However, some data samples in the WGS data obtained from the open data release 25 of ICGC are essentially reduced to WES-equivalent data as they do not contain any somatic mutations from the intergenic regions of the human genome. The following simple heuristic was used to eliminate such data samples: if in a given data sample the median SNV count across the 96 categories of SNV is less than 4, then such a data sample was excluded. (It should be noted that this simple heuristic may not be optimal, and including some data samples excluded based on this heuristic may improve statistical results.) Further, cancer types with fewer than 20 data samples were excluded to ensure nominal statistical significance of the resultant cancer genomic signatures.

The resultant data set had the following characteristics. The total number of cancer types N is 17. The total number of data samples M (across all 17 cancer types) is 3,392. (It should be noted that M is equal to the sum of $D_i$ over the N values of i.) Each data sample was labeled by an index c, where c takes M values. Each of the M data samples was treated in turn as a test data sample; for a test data sample labeled by a particular value of c, the remaining M−1=3,391 data samples were treated as training data samples, and the FLMs F[c][i] were computed using these 3,391 training data samples (i.e., the test data sample labeled by c is expressly excluded from the training data set used in computing F[c][i]). In this implementation of the diagnostic tool, all FLMs F[c][i] were defined to contain 3 columns computed (for each test data sample labeled by c) as the quantities μ[c][i], σ[c][i] and β3[c] defined above.

For each test data sample (labeled by c), 96-component working vector y[c] was computed as described above. Then, for each of the N cancer types i represented by the FLMs F[c][i], a regression of working vector y[c] against F[c][i], with the intercept, was run and a regression residual was computed as a 96-component vector z[c][i]. For each cancer type i, using working vector y[c] and residual vector z[c][i], composite parameter E1[c][i] was computed (by averaging modified R-squared parameters E[c][i, j] across the six channels j with uniform weights) as described above. The diagnosed cancer type for the test data sample labeled by c was then identified as the cancer type i that produced the largest E1[c][i], as described above.

FIG. 5 shows a table 500 with representative results from this analysis. Column 502 lists the resultant cancer types. For each cancer type, column 504 provides a descriptor of whether the cancer type corresponds to an organ level or subtype granularity level (as described above), and column 506 shows the corresponding number D of data samples. For each cancer type, column 508 shows the number of data samples with correctly diagnosed cancer type, and column 510 shows the corresponding percentage. It should be noted that the data includes two cancer types with organs combined. Thus, ICGC data is provided for the cancer type "colorectal cancer", which corresponds to two different organs: colon and rectum. Further, ICGC data is provided separately for esophageal adenocarcinoma and gastric cancer and then the data samples for these cancer types are combined under a single cancer type. This is done because the cancer genomic signatures for gastric cancer are very similar to those for esophageal adenocarcinoma and, consequently, in this implementation of the diagnostic tool, treating these as separate cancer types resulted in a large fraction of gastric cancer data samples (18 out of 31, or approximately 58%) that were misidentified as esophageal adenocarcinoma data samples. It should be noted that, in contrast, a smaller fraction of the esophageal adenocarcinoma data samples (26 out of 265, or less than 10%) were misidentified as gastric cancer data samples. Combining these two cancer types is justifiable as (similarly to colon and rectum), esophagus and stomach cancers are closely related due to the immediate interconnectedness of these two organs. It should also be noted that, in a small fraction of cases, melanoma can occur in parts of the body other than skin. However, all melanoma data samples in Table 1 corresponds to skin melanoma.

This example is intended to demonstrate that diagnostic tools of the type described herein can successfully distinguish different cancer types based on cancer genomic signatures as represented by using FLMs. It is not intended to limit the scope of the claimed invention to any particular cancer types or cancer genomic signatures.

While the invention has been described with reference to specific embodiments, those skilled in the art will recognize that variations and modifications are possible. As noted above, the training process can apply any number of different scaling functions to the SNV counts, and different statistical computations can be used to generate a library of FLMs for the cancer types to be distinguished, provided that the same scaling function applied to the SNV counts during training is also applied to the SNV counts of the test data sample during the diagnostic process. Scaling functions that are based on logarithms of the SNV counts may be preferred, due to the expected distribution of count values in the presence of noise. In some embodiments, multiple different mathematical functions can be used as scaling functions in parallel, with the results being combined (e.g., added together with uniform or nonuniform weights) to generate a final diagnosis.

In some embodiments, it is possible that the result may be ambiguous in some instances. For instance, two different cancer types i may yield the same E1[i] value that turns out to be the maximum across the cancer types. In such instances, the process is still useful to narrow down the cancer type. It should be noted that for realistic datasets with sufficiently large numbers of training data samples for each cancer type, such ambiguities are unlikely to arise within machine (computational) or any other reasonable preset precision. However, it should be noted that, depending on data availability, some cancer subtypes may have similar cancer genomic signatures making them difficult to distinguish (e.g., test data samples for a first cancer subtype are frequently misidentified as belonging to a second cancer subtype and vice versa). In such cases it may be desirable and reasonable to combine training data samples for such subtypes under the same type corresponding to the organ of origin and identify the organ of origin instead. It should further be noted that, depending on data availability, some organs of origin may have similar cancer genomic signatures making them difficult to distinguish (e.g., test data samples for a first organ of origin are frequently misidentified as belonging to a second organ of origin and vice versa). In such cases it may be desirable and reasonable to combine training data samples for such organs of origin under a single cancer type which includes two or more of such organs of origin and identify that cancer type instead, as long as such aggregation is justifiable (e.g., combining colon and rectal cancers, or combining gastric and esophageal cancers).

The set of cancer types to be distinguished can be varied, e.g., based on available training data. It is assumed that different cancer types will exhibit different patterns of SNVs, and it is these differences that the processes described herein attempt to detect. However, it is not necessary to associate the SNVs with particular genes or to identify biological mechanisms explaining the relation between particular patterns of SNVs and cancer types.

In embodiments described herein, it is assumed that, prior to performing diagnostic process 300, it is already known that a patient has cancer and that the diagnostic process is used to distinguish among different types of cancer, rather than cancer versus no-cancer. It may also be possible to use diagnostic process 300 to conclude that the patient likely does not have a cancer of any of the types tested. For example, if the largest E1[i] computed at block 314 is below a threshold, this may be an indication that the patient does not have any of the cancer types tested. (Cancer of an untested type, however, may be present.) In practice there may arise cases where, prior to using diagnostic process 300, a patient may be believed to have cancer based on other indicators (e.g., ctDNA levels in blood) due to a false positive. If diagnostic process 300 indicates that the patient does not have any of the cancer types tested, this may prompt a reevaluation of the prior cancer diagnosis and unveil the aforesaid false positive.

In some embodiments, one of the cancer types can be a "null" type (based on data from patients with no cancer), although it is expected that the null type would have a random pattern of SNVs and as such may not be particularly meaningful for determining the cancer type. However, it can still be useful to rule out cancer or cancer types tested, or to further filter out noise.

Tumor DNA samples, from which data used in the processes described herein is derived, can be extracted from any tissue of a patient, including blood, saliva, urine, plasma, or a specific organ or tissue. Any DNA sequencing techniques can be used, provided that the full or essentially full genome is covered and SNVs can be counted. (As described above, for some cancer types exome data can be useful.) The processes described herein do not require any knowledge of the source of the tumor DNA, as it is assumed that the SNV pattern associated with a cancer type does not depend on where the tumor DNA was extracted from.

The foregoing description also makes reference to matrices having columns and/or rows. Those skilled in the art will appreciate that matrix notation is a matter of convention and that rows and columns can be interchanged; all computations described herein can be performed with matrices in either row-wise or column-wise orientation, and a vector can be represented as a matrix with a single column or row. Accordingly, the terms "row" and "column" should be understood as merely denoting a first and second dimension of a matrix.

Various features described herein, e.g., methods, apparatus, computer-readable media and the like, can be realized using any combination of dedicated components and/or programmable processors and/or other programmable devices. The various processes described herein can be implemented on the same processor or different processors in any combination. Where components are described as being configured to perform certain operations, such configuration can be accomplished, e.g., by designing electronic circuits to perform the operation, by programming programmable electronic circuits (such as microprocessors) to perform the operation, or any combination thereof. Further, while the embodiments described above may make reference to specific hardware and software components, those skilled in the art will appreciate that different combinations of hardware and/or software components may also be used and that particular operations described as being implemented in hardware might also be implemented in software or vice versa.

Computer programs incorporating various features described herein, which may be implemented in any suitable programming language, may be encoded and stored on various computer readable storage media; suitable media include magnetic disk or tape, optical storage media such as compact disk (CD) or DVD (digital versatile disk), flash memory, and other non-transitory media. Computer readable

What is claimed is:

1. A method for diagnosing a cancer type based on genomic tumor DNA sequence data, the method comprising:
  defining a set of categories of somatic single nucleotide variations (SNVs);
  defining a set of cancer types;
  obtaining a training data set consisting of a plurality of data samples corresponding to a plurality of patients previously diagnosed with cancer, each data sample in the training data set including an SNV count vector that indicates a count of the number of instances of each of the categories of SNV detected in a genomic tumor DNA sequence for the patient and an identifier of a cancer type previously diagnosed for the patient, wherein each data sample in the training data set is assigned to exactly one of the cancer types;
  for each cancer type in the set of cancer types, constructing a working matrix from the training data set, wherein the working matrix includes a column corresponding to the SNV count vector for each data sample identified with the cancer type and wherein constructing the working matrix includes applying a scaling function to each of the SNV count vectors;
  for each cancer type in the set of cancer types, constructing a factor loading matrix based on the working matrices, wherein the factor loading matrix includes a number of columns, each column corresponding to a different statistical quantity computed from one or more of the working matrices;
  obtaining a test data sample, the test data sample including an SNV count vector that indicates a count of the number of instances of each of the categories of SNV detected in a genomic tumor DNA sequence for a patient to be diagnosed;
  applying the scaling function to the SNV count vector for the test data sample to generate a working vector;
  performing a regression analysis on the working vector against each of the factor loading matrices; and
  determining a cancer type for the test data sample based on a result of the regression analysis.

2. The method of claim 1 wherein the set of cancer types is defined based at least in part on an organ or tissue of origin.

3. The method of claim 1 wherein the set of cancer types includes at least two different cancer subtypes associated with a same organ or tissue of origin.

4. The method of claim 1 wherein the scaling function is a logarithmic scaling function.

5. The method of claim 1 wherein the scaling function is a trivial scaling function that leaves the SNV count vector unaltered.

6. The method of claim 1 wherein constructing the factor loading matrix for each of the cancer types includes:
  constructing a first column by computing a mean value of each row of the working matrix for the cancer type;
  constructing a second column by computing a standard deviation for each row of the working matrix for the cancer type; and
  constructing a third column by:
    computing, for each cancer type, an intermediate vector having as components the ratio of (i) the mean value of each row of the working matrix for the cancer type to (ii) the standard deviation for each row of the working matrix for the cancer type;
    forming an intermediate matrix whose columns are the intermediate vectors for each cancer type; and
    computing a final vector whose components are the mean value of each row of the intermediate matrix, wherein the same final vector is used as the third column of the factor loading matrix for each cancer type.

7. The method of claim 6 wherein, for at least one of the cancer types, at least one column of the factor loading matrix corresponds to a principal component of a covariance or correlation matrix computed from the intermediate matrix.

8. The method of claim 1 wherein, for at least one of the cancer types, at least one column of the factor loading matrix corresponds to a principal component of a covariance or correlation matrix computed from the working matrix for that cancer type.

9. The method of claim 1 wherein a first one of the factor loading matrices has a first number of columns, a second one of the factor loading matrices has a second number of columns, the second number being different from the first number.

10. The method of claim 1 wherein performing the regression analysis includes:
  for each cancer type in the set of cancer types:
    running a regression on the scaled test count vector against the factor loading matrix for the cancer type;
    computing, from each regression, a residual vector;
    computing a set of modified R-squared parameters for the regression, wherein the set of modified R-squared parameters is computed by grouping the SNV counts into a smaller number of SNV channels corresponding to a set of distinct base mutations; and
    computing a composite parameter from the set of modified R-squared parameters,
  wherein diagnosing the cancer type for the test data sample is based at least in part on the composite parameter computed for each cancer type.

11. The method of claim 10 wherein, for each cancer type, computing the composite parameter includes computing a mean value of the set of modified R-squared parameters computed for that cancer type.

12. The method of claim 11 wherein diagnosing the cancer type for the test data sample includes:
  comparing values of the composite parameters computed for each cancer type to identify a largest value; and
  identifying, as a most likely cancer type for the test data sample, the cancer type having the largest value of the composite parameter.

13. A method for diagnosing a cancer type based on genomic tumor DNA sequence data, the method comprising:
  defining a set of categories of somatic single nucleotide variations (SNVs);
  defining a set of cancer types;
  obtaining a training data set consisting of a plurality of data samples corresponding to a plurality of patients previously diagnosed with cancer, each data sample in the training data set including an SNV count vector that indicates a count of the number of instances of each of the categories of SNVs detected in a genomic tumor DNA sequence for the patient and an identifier of a cancer type previously diagnosed for the patient, wherein each data sample in the training data set is assigned to exactly one of the cancer types;
  for each cancer type in the set of cancer types, constructing a set of two or more working matrices from the training data set, wherein each working matrix includes a column corresponding to the SNV count vector for each data sample identified with the cancer type and wherein constructing each working matrix in the set of working matrices includes applying a different one of a set of scaling functions to each of the SNV count vectors;
  for each scaling function in the set of scaling functions, constructing a corresponding set of factor loading matrices, wherein each set of factor loading matrices includes one factor loading matrix for each cancer type in the set of cancer types, wherein each factor loading matrix includes a number of columns, each column corresponding to a different statistical quantity computed from one or more of the working matrices that were generated using the corresponding scaling function;
  obtaining a test data sample, the test data sample including an SNV count vector that indicates a count of the number of instances of each of the categories of SNV detected in a genomic tumor DNA sequence for a patient to be diagnosed;
  generating a set of scaled test count vectors by separately applying each of the set of scaling functions to the SNV count vector for the test data sample;
  performing a set of regression analyses on the set of scaled test count vectors, wherein performing the set of regression analyses includes performing a regression analysis on each of the scaled test count vectors against the one of the sets of factor loading matrices that corresponds to the same one of the scaling functions that was used to generate the scaled test count vector; and
  determining a cancer type for the test data sample based on a result of the set of regression analyses.

14. The method of claim 13 wherein the set of cancer types is defined based at least in part on an organ or tissue of origin.

15. The method of claim 13 wherein the set of cancer types includes at least two different cancer subtypes associated with a same organ or tissue of origin.

16. The method of claim 13 wherein one of the scaling functions in the set of scaling functions is a logarithmic scaling function.

17. The method of claim 13 wherein one of the scaling functions in the set of scaling functions is a trivial scaling function that leaves the SNV count vector unaltered.

18. The method of claim 13 wherein constructing at least one of the sets of factor loading matrices includes, for each of the cancer types:
  constructing a first column by computing a mean value of each row of the corresponding working matrix for the cancer type;
  constructing a second column by computing a standard deviation for each row of the corresponding working matrix for the cancer type; and
  constructing a third column by:
    computing, for each cancer type, an intermediate vector having as components the ratio of (i) the mean value of each row of the corresponding working matrix for the cancer type to (ii) the standard deviation for each row of the corresponding working matrix for the cancer type;
    forming an intermediate matrix whose columns are the intermediate vectors for each cancer type; and
    computing a final vector whose components are the mean value of each row of the intermediate matrix, wherein the same final vector is used as the third column of the factor loading matrix for each cancer type.

19. The method of claim 18 wherein, for at least one of the cancer types, at least one column of the factor loading matrix in at least one of the sets of factor loading matrices corresponds to a principal component of a covariance or correlation matrix computed from the intermediate matrix.

20. The method of claim 13 wherein, for at least one of the cancer types, at least one column of the factor loading matrix in at least one of the sets of factor loading matrices corresponds to a principal component of a covariance or correlation matrix computed from the working matrix for that cancer type.

21. The method of claim 13 wherein, within at least one of the sets of factor loading matrices, a first one of the factor loading matrices has a first number of columns, a second one of the factor loading matrices has a second number of columns, the second number being different from the first number.

22. The method of claim 13 wherein performing the set of regression analyses includes:
  for each scaled test count vector in the set of test count vectors and for each cancer type in the set of cancer types:
    running a regression on the scaled test count vector against the factor loading matrix for the cancer type from the set of factor loading matrices that corresponds to the same one of the scaling functions that was used to generate the scaled test count vector;
    computing, from each regression, a residual vector;
    computing a set of modified R-squared parameters for the regression, wherein the set of modified R-squared parameters is computed by grouping the SNV counts into a smaller number of SNV channels corresponding to a set of distinct base mutations; and
    computing a first composite parameter from the set of modified R-squared parameters; and
  for each cancer type, computing a second composite parameter from the first composite parameters computed for each scaled test count vector and that cancer type,
  wherein diagnosing the cancer type for the test data sample is based at least in part on the second composite parameter computed for each cancer type.

23. The method of claim 22 wherein, for each scaled test count vector and for each cancer type, computing the first composite parameter includes computing a mean value of the set of modified R-squared parameters computed for that cancer type.

24. The method of claim 23 wherein, for each cancer type, computing the second composite parameter includes computing a sum of the first composite parameters computed for that cancer type using each scaled test count vector.

25. The method of claim 24 wherein diagnosing the cancer type for the test data sample includes:
  comparing values of the second composite parameters computed for each cancer type to identify a largest value; and
  identifying, as a most likely cancer type for the test data sample, the cancer type having the largest value of the second composite parameter.

* * * * *

UNITED STATES PATENT AND TRADEMARK OFFICE
CERTIFICATE OF CORRECTION

PATENT NO.       : 10,685,738 B1
APPLICATION NO.  : 15/709407
DATED            : June 16, 2020
INVENTOR(S)      : Zurab Kakushadze Page 1 of 2

It is certified that error appears in the above-identified patent and that said Letters Patent is hereby corrected as shown below:

In the Specification

Column 2, Line 48: after "N cancer types, a" replace "96×D," with --96×$D_i$--.

Column 2, Line 63: after "96-component vector" replace "σ[i]" with --μ[i]--.

Column 7, Line 32: after "Principal Components" replace "{Q2[i][i]," with --{Q2[i][1],--.

Column 7, Line 40: after "i.e., just" replace "Q2[i][i]" with --Q2[i][1]--.

Column 7, Line 50: after "e.g.," replace "β[i]" with --μ[i]--.

Column 7, Line 65: after "FLM F[i] includes" replace "p[i]" with --μ[i]--.

Column 8, Line 8: after "consisting of the" replace "NFLMs" with --N FLMs--.

Column 9, Line 8: replace "component))," with --component $y_a$--.

Column 9, Line 30: after "16 components" replace "yc[j]k" with --yc[j]$_k$--.

Column 9, Line 32: after "the quantity" replace "(yc[j]k" with --(yc[j]$_k$--.

Column 9, Line 33: after "16 components" replace "yc[j]k" with --yc[j]$_k$--.

Column 9, Lines 37-38: after "the quantity" replace "(zc[i,j]k)$^2$" with --(zc[i,j]$_k$)$^2$--.

Column 10, Line 29: after "of such vectors is" replace "D." with --$D_i$--.

Column 11, Line 23: after "Tentative cancer type" replace "it" with --i1--.

Signed and Sealed this
Eighteenth Day of August, 2020

Andrei Iancu
*Director of the United States Patent and Trademark Office*

CERTIFICATE OF CORRECTION (continued)
U.S. Pat. No. 10,685,738 B1

Column 11, Lines 48-49: after "defined as" replace "$yy_a = 1n+1)$" with --$yy_a = \ln(y_a + 1)$--.

Column 11, Line 55: after "yields the largest" replace "EE1[1]" with --EE1[i]--.

Column 11, Lines 57-58: after "the largest sum of" replace "E1+EE1[1]" with --E1[i]+EE1[i]--.

Column 11, Line 66: after "E1[i] and" replace "EE1[1])" with --EE1[i])--.

Column 12, Line 3: after "E1[i] and" replace "EE1[1])," with --EE1[i]),--.

Column 14, Line 42: after "the corresponding number" replace "D" with --$D_i$--.